United States Patent [19]
Rocklin et al.

[11] Patent Number: 5,296,115
[45] Date of Patent: Mar. 22, 1994

[54] METHOD AND APPARATUS FOR IMPROVED DETECTION OF IONIC SPECIES BY CAPILLARY ELECTROPHORESIS

[75] Inventors: Roy D. Rocklin, Sunnyvale; Christopher A. Pohl, Union City; John Stillian, Pleasanton; Neboisa Avdalovic, San Jose, all of Calif.

[73] Assignee: Dionex Corporation, Sunnyvale, Calif.

[21] Appl. No.: 771,336

[22] Filed: Oct. 4, 1991

[51] Int. Cl.⁵ .................... G01N 27/26; G01N 27/447
[52] U.S. Cl. .............................. 204/180.1; 204/299 R
[58] Field of Search ..................... 204/180.1, 299 R

[56] References Cited

FOREIGN PATENT DOCUMENTS 345782 12/1989 European Pat. Off. .

Primary Examiner—John Niebling
Assistant Examiner—John S. Starsiak, Jr.
Attorney, Agent, or Firm—Flehr, Hohbach, Test, Albritton & Herbert

[57] ABSTRACT

Apparatus and methods are provided for increasing the sensitivity of detection of ionic species separated by capillary electrophoresis. The apparatus includes capillary electrophoretic separating means, suppressor means and detector means.

10 Claims, 3 Drawing Sheets

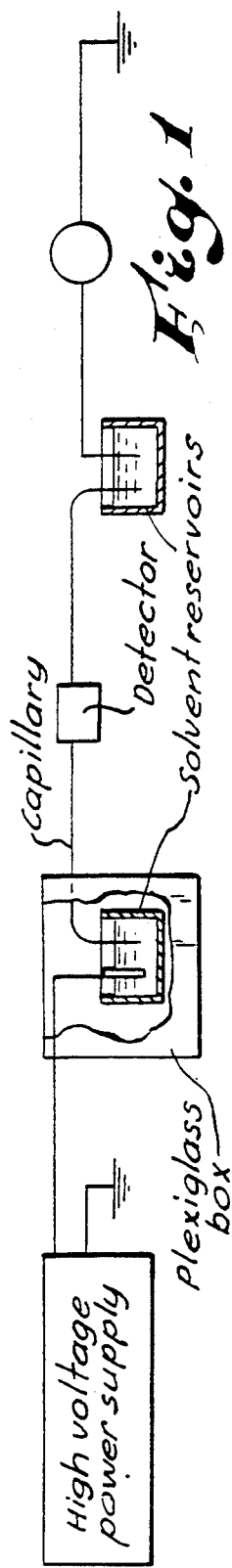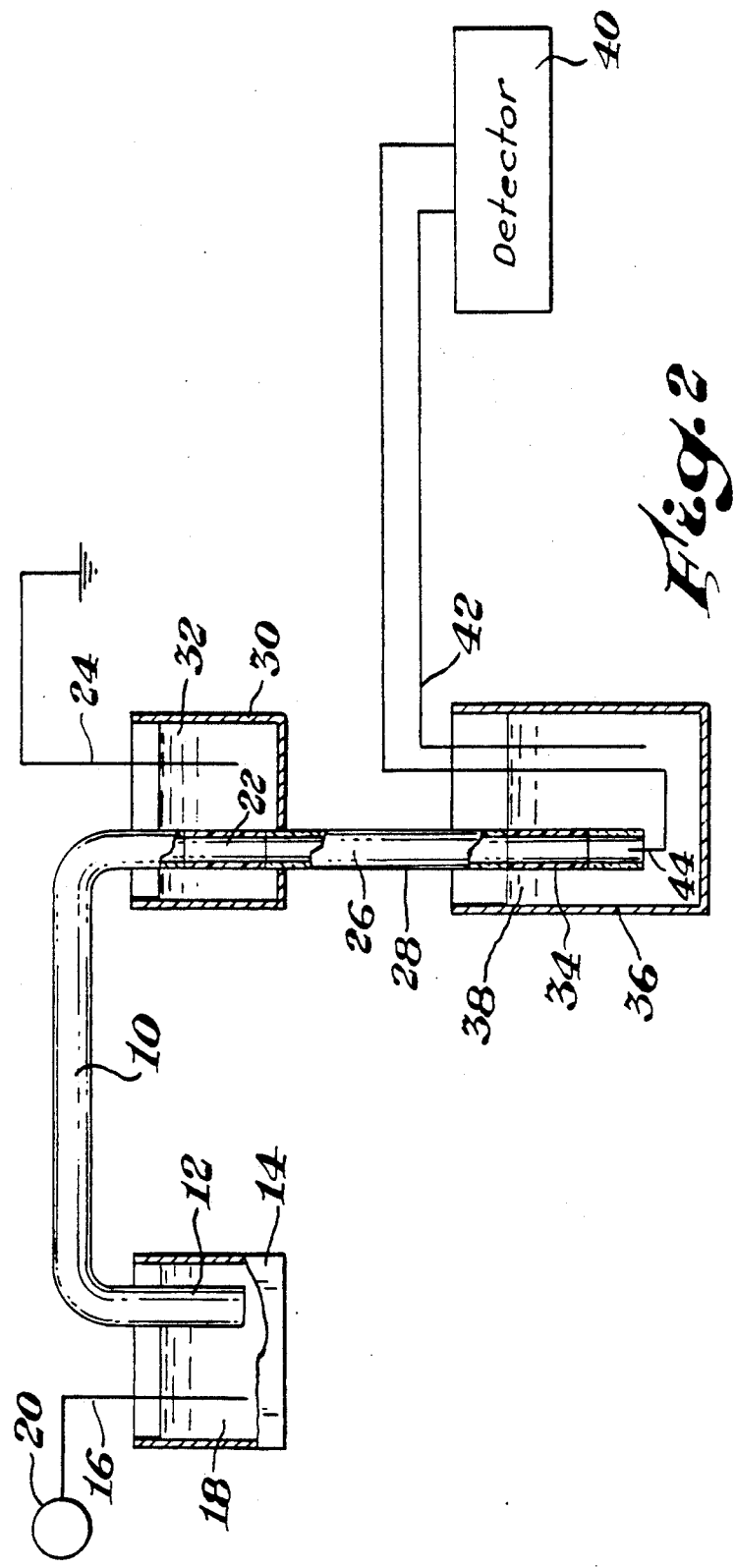

METHOD AND APPARATUS FOR IMPROVED DETECTION OF IONIC SPECIES BY CAPILLARY ELECTROPHORESIS

FIELD OF THE INVENTION

The present invention relates to method and apparatus using capillary electrophoresis and ion suppression for the determination of anions or cations.

BACKGROUND OF THE INVENTION

Capillary electrophoresis is a known technique involving electrophoresis in small bore capillaries. This approach provides methods for efficient analytical separations of ionic species including macromolecules. A typical capillary electrophoresis system is shown in FIG. 1. As can be seen, a capillary is positioned between two solvent reservoirs containing electrolyte. Electrodes present in each of the reservoirs and coupled to a power supply capable of delivering upwards to 30 kV per 100 cm of capillary provide a voltage gradient to drive charged species through the capillary bore. A detector is positioned at a point between the two high voltage electrodes to permit detection of various ionic species migrating in the capillary. A detector so positioned is sometimes referred to as an on-column detector.

A number of approaches have been developed to detect the solutes separated by capillary electrophoresis depending, in part, upon the nature of the solute detected. UV absorption and fluorescence have been the most commonly used detection modes. Mass spectrometric, radiometric and electrochemical methods of detection have also been utilized. With regard to electrochemical detection, amperometry and conductivity methods have been used.

Off-column amperometric detection utilizing a porous glass capillary to cover a crack in the capillary has also been reported. Wallingford, R. A., et al., *Anal. Chem.* (1987) 59, 1762-1766; Ewing, A. G., et al., *Anal. Chem.* (1989) 61, 292A-303A. End-column amperometry and conductivity detection have also been performed. Huang, et al., *Anal. chem.* (1991), 63, 189-192. A significant problem with on-column and end-column detection utilizing electrochemical techniques is the effect of the high voltage applied to the electrodes to generate the voltage gradient across the capillary. Small variations in this high voltage gradient (typically ranging from 20-30 kV) have significant impact upon the voltages used for amperometric detection and conductivity detection which generally utilizes less than 1 volt in such detection systems.

Even for off-column electrochemical detection, a significant signal to noise problem exists due to the presence of relatively high concentrations of the electrolyte needed in the eluent to generate the voltage gradient across the length of the capillary bore. This is especially problematic for detection utilizing conductivity since such measurements are more significantly affected by electrolyte concentration than amperometric detection which is based primarily upon the detection of redox reactions at the detection electrodes.

Although electrolyte suppression has been used primarily in ion exchange chromatography in conjunction with conductivity detection (see e.g. U.S. Pat. Nos. 3,897,213 3, 3,920,397, 3,925,019, 3,956,559, 4,474,664, 4,751,004, 4,459,357 and 4,999,098), such suppressors have not been adapted for use with capillary electrophoresis.

The references discussed above are provided solely for their disclosure prior to the filing date of the present application and nothing herein is to be construed as an admission that the inventor is not entitled to antedate such disclosure by virtue of prior invention.

SUMMARY OF THE INVENTION

In accordance with the invention, apparatus and methods are provided for increasing the sensitivity of detection of ionic species separated by capillary electrophoresis. The apparatus includes capillary electrophoretic separating means, suppressor means and detector means. The capillary electrophoretic separator means typically include a small bore capillary having a first end in communication with a first electrolyte reservoir which also contains a first electrode means. The capillary also has a second end having an ion conduction means in communication with the second electrolyte reservoir containing a second electrode means. The first end of the capillary is capable of receiving electrolyte from the first reservoir which is present throughout the entire bore of the capillary. The ion conducting means at the second end of the capillary is capable of conducting current generated between the first and second electrodes when an electrolyte is present in said capillary and said first and said second reservoirs and a voltage is applied to the electrodes. This construction essentially isolates the suppressor means and detector means from the current and high voltage gradient generated between the two electrodes.

The suppressor means comprises at least one capillary effluent compartment having an inlet and an outlet end. The inlet end is in communication with the second end of the capillary in the capillary electrophoretic separating means. The suppressor means also contains at least one regenerant compartment means and at least one ion exchange member partitioning the capillary effluent compartment means and the regenerant compartment means. This ion exchange membrane is permeable to ions of the same charge (i.e., positive or negative) as the counter ion of the ionic species to be separated and impermeable to ions of the same charge as the ionic species to be separated.

The detector means of the apparatus is in communication with the outlet end of the suppressor means and is suitable for detecting resolved ionic species eluting therefrom.

In operation, the ionic species of the sample are separated in the bore of the capillary of the electrophoretic separating means by a voltage gradient generated by applying a voltage across the electrodes. The effluent from this separating means flows into the suppressor means and in particular the capillary effluent compartment means. The regenerant compartment means contains a regenerant which is dissociated into cations and anions. Since the ion exchange membrane partitioning the capillary effluent compartment and regenerant compartment is preferably permeable to ions of the same charge (i.e., positive or negative) as the counter ions of the ionic species to be detected, such counter ions are capable of crossing the membrane into the regenerant compartment. The regenerant ion of the same charge is capable of crossing the membrane from the regenerant compartment into the effluent in the capillary effluent compartment. The net effect is to exchange the counter ion of the ionic species of interest.

For example, if an anion is to be detected and the electrolyte is sodium hydroxide, a typical regenerant is sulfuric acid. For each molecule of electrolyte one sodium ion is replaced with a hydronium ion from the regenerant sulfuric acid to form water. Similarly, the sodium ion associated with the anionic species of interest is replaced with a hydronium ion from the regenerant solution. As a consequence, the overall conductivity of the eluent decreases and the overall conductivity of ionic species and counter ion increases. The thus treated effluent then flows to a detector. Since the overall concentration of electrolyte has been reduced, the sensitivity of detecting conductivity increases.

BRIEF DESCRIPTION OF THE DRAWINGS

FIG. 1 is a schematic diagram of a prior art apparatus for performing capillary electrophoresis derived from FIG. 1 of Ewing, et al., *Anal. Chem.* (1989), 61, 292A-303A.

FIG. 2 is a schematic diagram of one of the embodiments of the invention.

DETAILED DESCRIPTION OF THE PREFERRED EMBODIMENTS

Figure 3:
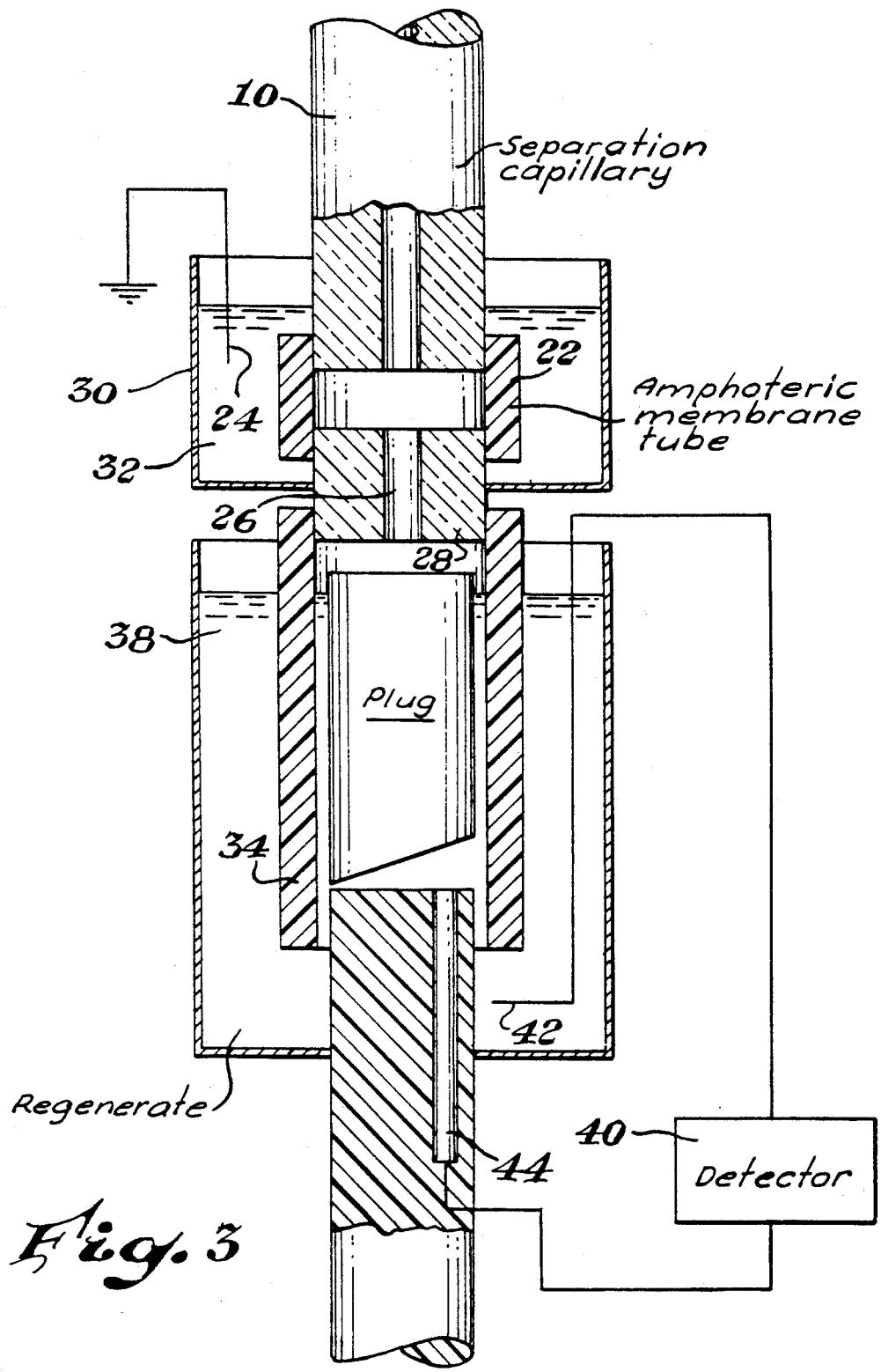
FIG. 3 is a schematic diagram of the ion conducting means and suppressor means used in Example 1.

The system of the present invention is useful for determining a large number of solutes so long as such solutes are anions or cations. A suitable sample includes surface waters and other liquids such as industrial chemical wastes, body fluids, beverages such as fruits and wines and drinking water. When the term "ionic species" is used herein, it includes species in ionic form and components of molecules which are ionizable under the conditions of the present system.

Generally, the ionic species which are particularly susceptible to detection by the apparatus and methods disclosed herein are those species that absorb visible or ultraviolet light only weakly and therefore are poorly detected by photometric absorbance detection. Examples of weakly absorbing species are common inorganic ions such as chloride, sulfate, sodium and potassium as well as many organic species such as acetate, succinate and trimethylamine.

As used herein, a "capillary electrophoretic separating means" refers to any means for separating ionic species which contains an elongate narrow bore through which an electrolyte can be passed and which has ends that can be placed in contact with first and second electrolyte reservoirs. Although in the preferred embodiments, typical narrow bore capillaries generally used in prior art devices are used, the term "capillary" is not limited to such capillaries. Rather, as used herein capillary refers to any elongate bore in a solid support having the dimensions on the order of magnitude of the internal dimensions of prior art capillary devices. Such capillaries have acceptable bore diameters ranging from 1 to 1000 $\mu$m, more preferably 25 to 100 $\mu$m. Generally, the length of such capillaries are about 1 cm to 10 meters, more preferably 20 cm to 100 cm. Based on these parameters, capillaries for use in practicing the present invention may comprise such capillaries or may comprise channels of irregular or regular shape formed in a solid support such as silica by etching or machining. In some instances it may be desired to form one side of a capillary in two separate blocks of solid support material which can thereafter be joined to form the complete capillary. In general, the cross-sectional area of such non-standard capillaries is substantially similar to that of conventional capillaries.

Referring to FIG. 2, a simplified apparatus for performing the present invention is illustrated. The system includes capillary 10 which contains a first end 12 immersed in an electrolyte reservoir 14. Also contained within this reservoir is first electrode 16 and an electrolyte 18. This first electrode 16 is connected to high voltage supply unit 20. The second end of the capillary 10 has an ion conduction means 22 attached thereto. This ion conduction means can be any conducting device that allows conduction of the current resulting from the high voltage current generated between electrodes 16 and 24 through capillary 10. Such conducting means, because of the use of suppressor means and detector downstream from the ion conduction means, requires that this ion conduction means be chosen such that a substantial amount of the mass flow through capillary 10 pass by ion conduction means 22 toward suppressor tube 34. One embodiment of conductive means comprises a gap between the capillaries with an insulating sleeve having one or more conducting holes. Alternatively, the insultaing sleeve may be loosely fitting to form an eluent gap between the capillaries and the sleeve. A further embodiment of the ion conduction means includes a capillary gap with a porous sleeve capable of conducting ions through the pores contained therein. Such gaps, pores or holes are used to provide a channel for ionic current between the eluent at the second end of capillary lo and the second electrode 24 and should be chosen such that at least about 50% of the mass flow passes such conducting means to remain in the downstream mass flow channel 26. In general, the nature of such gaps, holes or pores should be large enough to provide sufficient ionic current to complete the high voltage circuit but not be so large as to allow the eluent to be diverted into reservoir 30.

In the preferred embodiments, the ion conductivity means 22 is an amphoteric membrane, preferably a sleeve which is capable of engaging the second end of capillary 10 and an end of downstream conduit 28. A specific method for producing such an amphoteric membrane sleeve is disclosed in Example 1. Other methods will be readily apparent to those skilled in the art and basically involve derivitizing a membrane with both anionic and cationic functional groups.

The second reservoir 30 also contains an electrolyte 32 which is in contact with the second electrode 24 and the ionic conduction means 22 to complete the high voltage circuit. As a consequence, the voltage drop along the remaining flow path to the detector is negligible.

In general, the electrolyte present in at least the first reservoir and the capillary bore is dependent upon the ionic species to be detected. When the ionic species is an anion, the electrolyte is preferably the salt form of a weak acid. Examples include sodium borate, sodium carbonate and sodium hydorxide. When the ionic species to be detected is a cation, the electrolyte is preferably the salt form of a weak base. An example of such an electrolyte is hydrogen chloride.

An important aspect of practicing the invention, however, involves the proper choice of voltage to be applied across the electrophoresis electrodes 16 and 24.

Since a high voltage circuit is produced between electrode 16 and electrode 24 via the ionic conducting means 22 and electrolyte solution 32, there is no voltage potential downstream from ionic conducting means 22 to drive the ionic species and the electrolyte into the suppressor means. To overcome this problem, the voltage is chosen such that it induces an electroendosmotic flow in the direction from the first reservoir to the detector. Electroendosmotic flow is generated primarily because of a local voltage which exists at the interface between the inside surface of the capillary and the electrolyte solution. This potential, sometimes referred to as the zeta potential, is dependent upon the material forming the inside surface of the capillary and the solution in contact with this surface.

In a silica capillary the charge on the inside wall of the capillary is negative and the direction of electroendosmotic flow is toward the negative electrode or away from the positive electrode. It is possible to reverse the direction of electroendosmotic flow by coating or derivatizing the wall of the silica capillary such that the charge on the wall is positive instead of negative. Under such circumstances to ensure electroendosmotic flow to the detector, the polarity of the electrode in the first reservoir should be reversed. It is also possible to use capillaries made of materials such as polyethylene or polystyrene that have no surface charge. These materials can then be functionalized to generate a positive or negative charge for example by quanternization or sulfonation respectively using known chemistries. The major reason for controlling electroendosmotic flow is to control separation resolution of the ionic species being separated. If the electroendosmotic flow is the same direction as the electrophoretic direction of the ionic species the separation resolution is less than when the electroendosmotic flow is in the opposite direction of the electrophoretic direction.

The downstream connector 28 is connected to a suppressor tube 34 contained in a regenerant compartment 36. The regenerant compartment 36 contains a regenerant 38 appropriate for the ionic species to be detected and the electrolyte used for capillary electrophoresis.

The suppressor tube 34 has an internal bore which forms a compartment to contain the effluent from the capillary 10. The inlet portion of this capillary effluent compartment is connected to downstream conduit means 28. An ion exchange membrane is positioned between this capillary effluent and the regenerant compartment. In general, suppressor tube 34 comprises an ion exchange membrane to facilitate ionic transport between the capillary effluent compartment and the regenerant compartment. The ion exchange membrane is chosen such that it is preferentially permeable to the counter ion of the ionic species. Thus, if the ionic species is an anion its counter ion is a cation. The ion exchange membrane is chosen to be permeable to cations. The converse is also true. Such tubular membranes can be purchased commercially such as the cation exchange membrane tube Nafion ® available from Perma Pure Products, Toms River, N.J. It is to be understood, however, that the suppressor means need not be a tubular form of an ion exchange membrane. Alternate embodiments include flat membranes such as that disclosed in U.S. Pat. No. 4,999,098 incorporated herein by reference.

Although it is preferable that the cross-sectional area of the downstream conduit 28 be the same as that of the cross-sectional area of the bore of capillary 10 and further that the cross-sectional area of the capillary effluent compartment 34 have substantially the same cross-sectional area, it is not necessary that such cross-sectional areas be the same. Useful results have been obtained where the inside diameter of the circular bore capillary 10 was 75 microns and the inside diameter of the Nafion ® cation exchange membrane tube was 400 microns. However, these results can be further improved when a 350 $\mu$m diameter plug is inserted inside the Nafion ® tube to reduce the effective cross-sectional flow area of the ion suppressor (see Example 1).

The suppressor length should be suffiecient to exchange cations or anions in the effluent but not be so long as to result in substantial band broadening. Such suppressor length can be from 100 $\mu$m to 10 cm, preferably 1 mm to 1 cm.

The foregoing describes a passive diffusion suppressor means for reducing electrolyte concentration. However, any suppressor system can be used in practicing the invention including those utilizing the application of electrical fields across the ion exchange membrane to increase the rate of ion exchange above that which would otherwise be obtained by diffusion limited exchange kinetics. See e.g. U.S. Pat. No. 4,999,098 incorporated herein by reference.

After passing the ion exchange membrane, the thus treated effluent is substantially depleted in the electrolyte and counter ions to the ionic species of interest. Such treated effluent may be directed to a flow through conductivity cell for detection of the ionic species present. Alternatively, one or both of the detection electrodes 42 and 44 can be inserted into the treated effluent stream exiting the suppressor means. When used in this manner, the outlet of the suppressor means may be maintained in the regenerant solution 38 provided the electrodes are positioned sufficiently within this end region so that conductivity is not adversely influenced by diffusion of regenerant ions into the effluent stream. In general, when one or more of the electrodes are inserted into the suppressor means outlet, the linear flow rate of the effluent should be sufficient to offset the potential diffusion of the regenerant ions into the effluent stream which would otherwise defeat the purpose of the suppressor means.

Although the foregoing has described the invention primarily within the context of open-tube capillary zone electrophoresis, it is believed that other modes of capillary electrophoresis may be practiced using the invention. Such other modes include isotachophoresis, micellar electrokinetic capillary chromatography, capillary gel electrophoresis and isoelectric focusing.

The following sets forth a specific embodiment of the invention and is not to be construed as a limitation of the claims as appended hereto.

EXAMPLE 1

Referring to FIG. 3, the separation capillary 10 was a fused silica capillary with dimensions of 75 $\mu$m i.d., 375 $\mu$m o.d., and 75 cm length. It was butted up against a second fused silica capillary 28 of the same i.d. and o.d. but about 6 mm long. The amphoteric ion exchange membrane tube 22 with dimensions of about 400 $\mu$m i.d., 800 $\mu$m o.d., and about 1 cm long also acted as a sleeve to hold the two pieces of capillary 10 and 28 together. The amphoteric membrane sleeve was attached to the capillaries by tightly tying nylon monofilament (75 $\mu$m diameter) around the sleeve. The amphoteric membrane sleeve was made from a substrate tube made of polyethylene/polyvinyl acetate. This tube (Microline ®) was obtained from Thermal Plastic Scientific, Warren, N.J. It was radiation grafted with vinylbenzylchloride (VBC) to about 50% VBC by weight. The grafted tube was refluxed for 14 hours in a 1M solution of dimethylaminoacetonitrile in methanol and allowed to cool for 6 hours. Following rinses in methanol and water, the tube was heated to about 60° C. in 1M sodium hydroxide solution for 90 minutes. This reaction hydrolyzes the —CN to —$CO_2^-$. The resulting tube contains the following functional group covalently bonded to the VBC molecules in the membrane: —$N^+(CH_3)_2CH_2CO_2^-$.

The other end of capillary 28 was inserted into a length of Nafion ® cation exchange tubing with approximate dimensions of 400 μm i.d., 800 μm o.d., and 1 cm long (Perma Pure Products, Toms River, N.J.) which served as the suppressor 34. The suppressor was held onto capillary 28 by tying with Nylon monofilament. Much of the internal volume of the suppressor was taken up with a 350 μm o.d. by 5 mm long plug made from capillary with the ends sealed with epoxy resin. The approximate length of the suppressor from the exit of tube 28 to the detector electrode 44 was 6 mm. One of the detector electrodes 44 was made by inserting a 127 μm platinum wire into a 150 μm i.d., 350 μm o.d. by 2 cm long capillary and filling the remaining volume with epoxy resin. The face of the capillary was polished to expose the end of the platinum wire. This electrode was inserted about 1 mm inside the suppressor, and the other end of the wire was connected to the conductivity detector cables. The second detector electrode 42 was placed into the regenerant solution 38.

The electrolyte in both the first electrolyte reservoir and in the second electrolyte reservoir was a 10 mM borax solution, pH 9.1. The regenerant 38 was a 15 mM sulfuric acid solution.

Figure 4:
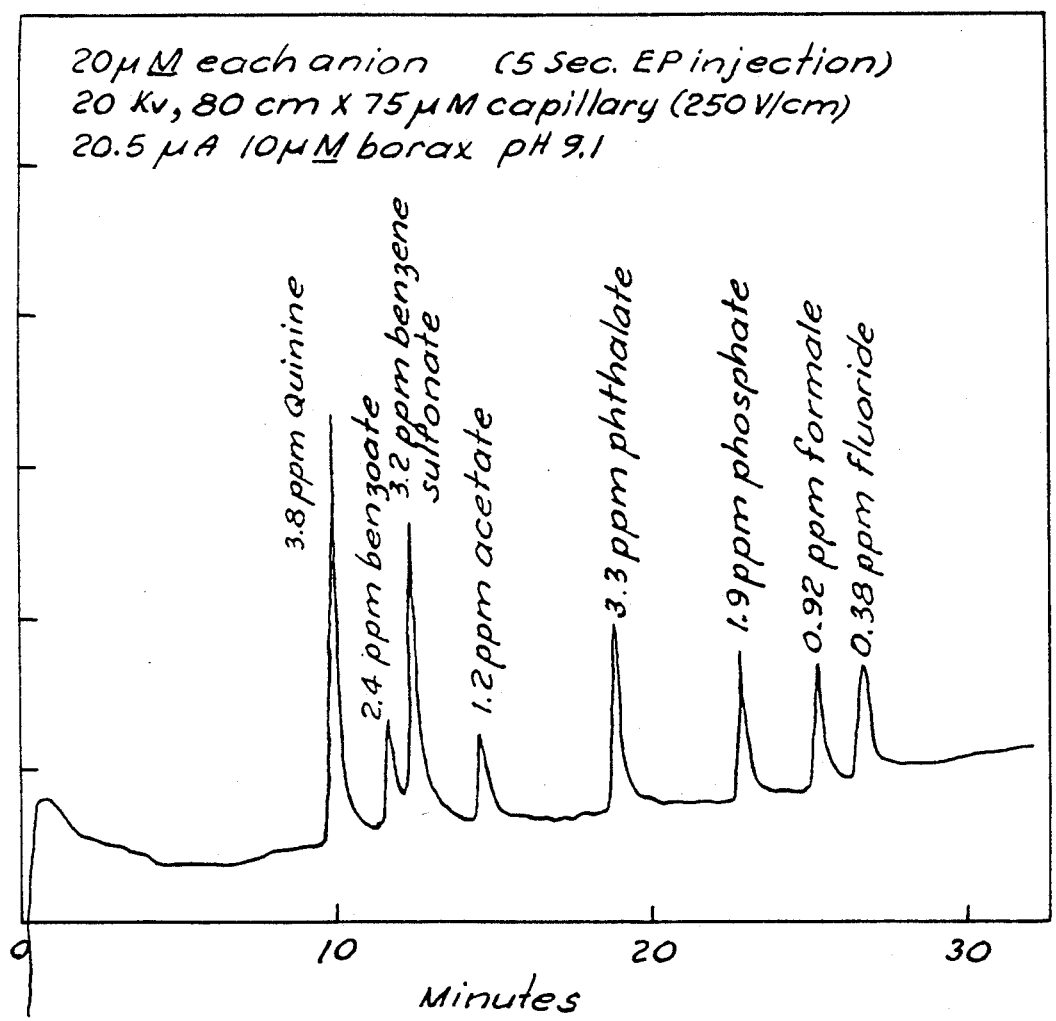
FIG. 4 is an electropherogram demonstrating the separation and detection of various anionic species by measuring conductivity using an embodiment of the invention.

The applied high-voltage was 20 kV, which resulted in a current of 20.5 μA. A 5 second electrophoretic injection was used to inject a sample of 20 μM each of the following anions: quinate, benzoate, benzenesulfonate, acetate, phthalate, phosphate, formate, and fluoride. The results are shown in FIG. 4.

Having described the preferred embodiments, it will be apparent to those skilled in the art that various modifications may be made to such embodiments and that such modifications are intended to be within the scope of the invention.

What is claimed is:

1. Apparatus for ion analysis comprising
  (a) capillary electrophoretic separating means for separating ionic species comprising a capillary having a first end in communication with a first electrolyte reservoir containing first electrode means and a second end having ion conduction means in communication with a second electrolyte reservoir having second electrode means, said first end of said capillary being capable of receiving electrolyte from said first reservoir and said ion conducting means at said second end of said capillary being capable of conducting the current generated between said first and said second electrodes when an electrolyte is present in said capillary and said first and said second reservoirs and a voltage is applied to said electrodes,
  (b) suppressor means for treating effluent eluted from said capillary electrophoretic separating means, said suppressor means including
    (1) at least one capillary effluent compartment means having an inlet end and an outlet end, said inlet end being in communication with said second end of said capillary,
    (2) at least one regenerant compartment means and
    (3) at least one ion exchange membrane partitioning said capillary effluent compartment means and said regenerant compartment means, said ion exchange membrane being preferentially permeable to the counter ion of said ionic species, and
  (c) detector means in communication with the outlet end of said suppressor means suitable for detecting resolved ionic species eluting therefrom.

2. The apparatus of claim 1 wherein said detector means comprise first and second spaced detection electrode means wherein at least one of said detection electrode means is in electrical communication with the effluent from said outlet end of said suppressor means.

3. The apparatus of claim 2 wherein said detecting of said resolved ionic species comprises measuring the conductivity of the effluent from said outlet end of said suppressor means.

4. The apparatus of claim 1 wherein said capillary effluent compartment and said ion exchange membrane in said suppressor means have substantially the same cross-sectional area.

5. The apparatus of claim 4 wherein said capillary and said selective ion exchange membrane tube have a circular cross section of substantially the same diameter.

6. The apparatus of claim 1 wherein said ion conduction means comprises an amphoteric ion exchange membrane.

7. A method of ion analysis comprising
  (a) passing a sample containing ionic species in an electrolyte solution, including transmembrane electrolyte ions of opposite charge to said ionic species, through capillary electrophoretic separating means in which said ionic species are separated and wherein said capillary electrophoretic separating means comprises a capillary having first and second ends wherein said first end is in contact with a first electrolyte reservoir containing electrolyte and first electrode means and said second end comprises ionic conduction means in communication with a second electrolyte reservoir containing electrolyte and second electrode means, said first and said second electrode means having a voltage applied thereto to cause the separation of said ionic species,
  (b) flowing the effluent from the capillary electrophoretic separating means through a suppressor means having at least one capillary effluent compartment means, at least one regenerant compartment means containing regenerant and at least one ion exchange membrane partitioning said capillary effluent and said regenerant compartment means, said ion exchange membrane being preferentially permeable to the counter ion of said ionic species to allow said counter ion to cross said membrane into said regenerant compartment means and regenerant ions of the same charge to pass said membrane into said effluent, and
  (c) flowing the treated effluent from the outlet of said capillary effluent compartment in said suppressor means through detection means in which said separated ionic species are detected by measuring the conductivity of said treated effluent.

8. The method of claim 7 wherein the voltage applied to said first and said second electrode means is sufficient to induce electroendosmotic flow through said capillary.

9. The method of claim 8 wherein said electroendosmotic flow is from said first end to said second end of said capillary, the internal surface of said capillary has a negative charge and said first electrode has a positive polarity as compared to said second electrode.

10. The method of claim 8 wherein said electroendosmotic flow is from said first end to said second end of said capillary, the internal surface of said capillary has a positive charge and said first electrode has a negative polarity as compared to said second electrode.

* * * * *